United States Patent [19]

Martin et al.

[11] Patent Number: 5,792,215
[45] Date of Patent: Aug. 11, 1998

[54] LASER INTEGRATED TARGETING AND ENTRY SYSTEM AND METHOD

[75] Inventors: David E. Martin; Phoebe A. Kaplan; Robert G. Dussault, all of Charlottesville, Va.

[73] Assignee: The University of Virginia Patent Foundation, Charlottesville, Va.

[21] Appl. No.: 715,626

[22] Filed: Sep. 18, 1996

Related U.S. Application Data

[60] Provisional application No. 60/003,907, Sep. 18, 1995.
[51] Int. Cl.$^6$ ........................................... A61N 21/00
[52] U.S. Cl. .................................... 607/89; 607/88
[58] Field of Search ..................... 607/89, 100, 112, 607/113, 88

[56] References Cited

U.S. PATENT DOCUMENTS

| | | | |
|---|---|---|---|
| 3,653,384 | 4/1972 | Swope | 607/89 |
| 4,697,590 | 10/1987 | Nakai et al. | 607/89 |
| 5,031,203 | 7/1991 | Trecha | 378/205 |
| 5,283,808 | 2/1994 | Cramer et al. | 378/206 |
| 5,305,759 | 4/1994 | Kaneko et al. | 607/89 |

*Primary Examiner*—Michael Powell Buiz
*Assistant Examiner*—Julian W. Woo
*Attorney, Agent, or Firm*—Oblon, Spivak, McClelland, Maier & Neustadt, P.C.

[57] ABSTRACT

A guidance system and method for accurately reproducing surgical approach angles for increasing the efficiency and accuracy of image-guided biopsy procedures which require high levels of precision with respect to the orientation of surgical instruments prior to insertion. A tri-axial structure mounted in the vicinity of the patient provides a laser light beam to the point of incision on the surface of a patient. The orientation of this laser light beam serves as a guide for not only the location of the entry point of the surgical instrument but also the orientation of the surgical instrument during insertion. A range finding structure positioned in parallel with the tri-axial mounted structure provides an indication of the depth of insertion of the surgical instrument.

5 Claims, 3 Drawing Sheets

LASER INTEGRATED TARGETING AND ENTRY SYSTEM AND METHOD

This is a non-provisional application based on provisional application Ser. No. 60/003,907 filed Sep. 18, 1995.

BACKGROUND OF THE INVENTION

1. Field of the Invention

The present invention relates to a guidance device and method for optimizing surgical entry into a patient and controlling the subsequent depth of insertion.

2. Discussion of the Background

Prior to a biopsy procedure, radiologist perform imaging by means of computer tomography (CT), plain film radiography, fluoroscopy and/or magnetic resonance imaging (MRI) to determine location, size and morphology of pathologic tissue or other structures in the body. These imaging procedures assist radiologists and surgeons in determining significant anatomical features surrounding lesions (e.g. nerves, blood vessels, etc.) which present obstacles to the excision of tissue. The information derived from these imaging techniques allows a physician to strategically plan a surgical approach which will optimize tissue sampling while simultaneously protecting collateral tissue.

With these images, it is possible to measure the angulation of the surgical approach and the lesion depths relative to cutaneous features on the body. Although the procedure of obtaining the images and subsequently detailing the angles of approach and the depth are quite precise, the execution of these procedures along with the determination of the approach angles and the penetration depth are in fact highly subjective. In order to provide any kind of precision, multiple images are required to confirm biopsy needle placement prior to tissue excision, which adds a significant amount of time and expense to the procedure. Ultimately, in these prior devices it is the skill of the physician which determines the efficiency of the biopsy procedure.

Recent approaches to further aid the surgeon include techniques in which a laser (typically HeNe) is placed over the patient at an orientation which matches the surgical path planned, based upon the initial localized images. These systems do not allow for any portability and are restricted in application to use with a CT machine. These devices include those reported by: Frederick P. R., et al (Radiology 154:535–6, 1985), Negata Y. et al (J. of Comp. Asst. Tomo. 14:1046–1048, 1990) and Miaux Y. et al ("Laser Guidance System for CP Guided Procedures") in Radiology 194:282–283, January 1995. Of these devices, the structures of Miaux and Negata were positioned on the CT gantry so that there was no room for the surgeon to move. Further none of these devices have any indication which would assist in the depth of penetration of the surgical tool.

In a typical procedure for performing a biopsy, a team of physicians and technologists, upon receiving the image information indicating an optimized approach angle, will rely on the use of a simple protractor held at the foot of a patient to estimate approach angles for performing the procedure. This highly subjective system requires many scans to ensure proper instrument placement prior to incision of the tissue. These images increase the time and expense of the entire procedure.

Furthermore, the existing guidance devices, as discussed above, do not allow for complete freedom of movement for the physician because they either have rigid frames attached near the patient's skin or they are positioned on a device which does not allow the physician to perform the procedure from anywhere along the length of the CT bed.

There is thus a need for a device which allows freedom of movement of the physicians while at the same time ensuring a quick and reliable and accurate positioning of surgical tools for subsequent entry into the body, based upon the desired angle of entry.

SUMMARY OF THE INVENTION

Accordingly, one object of the present invention is to provide a novel guidance system to replicate surgical approach angles to exactly match a preoperative approach plan with minimal need for presurgery imaging.

It is further object of the present invention to provide a multi-planar guidance system which increases the efficiency and accuracy of an image-guided biopsy procedure which can also be used in orthopaedic fixation and hardware placement in other surgical procedures in which the orientation of introduced instrumentation requires high levels of precision.

It is a further object of the present invention to provide an accurate multi-planar guidance system which also allows for precise measurement of the depth of introduced instruments into the body in accordance with a preoperative surgical approach.

It is a further object to the present invention to provide a method of tissue incision whereby surgical planning images of a patient are obtained and surgical angles are determined in a three-dimensional orthogonal plane. Subsequently, a light source provides a spot on the patient which coincides with the predetermined point of incision and, utilizing two ends of a surgical instrument, the angle of insertion is determined and, during insertion, the depth of insertion is monitored.

BRIEF DESCRIPTION OF THE DRAWINGS

For a more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
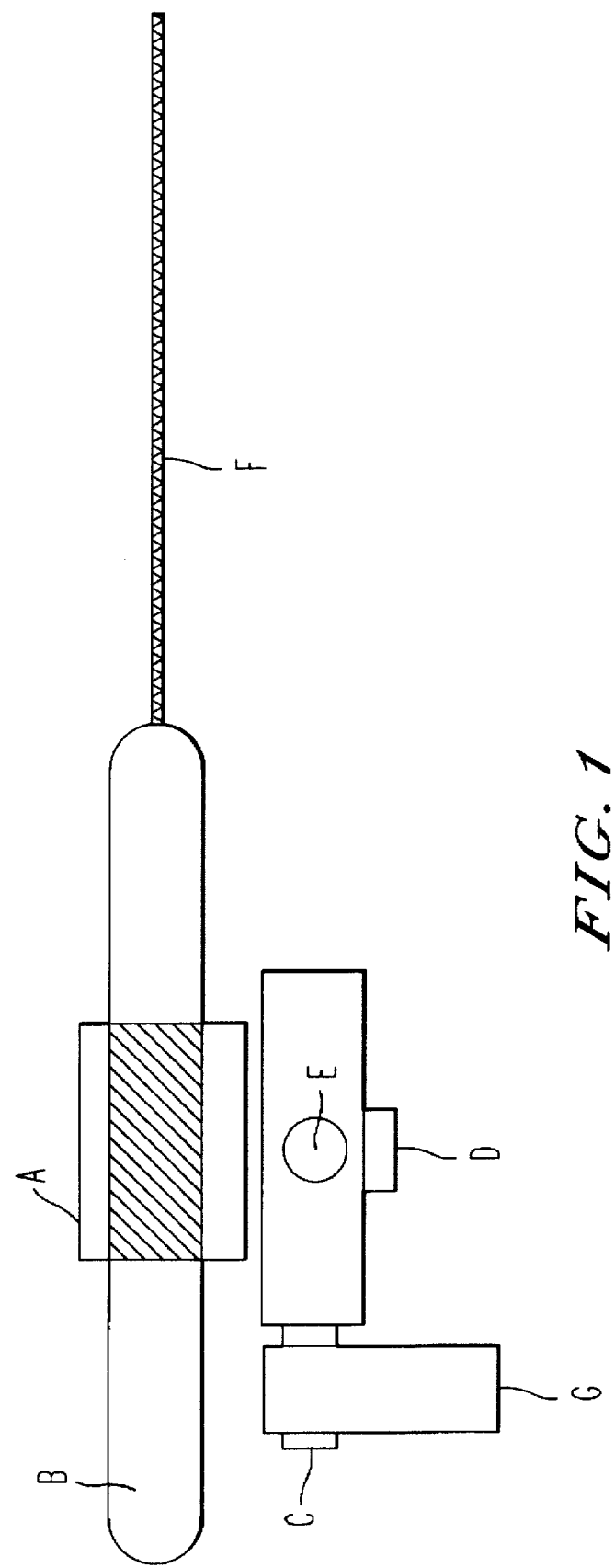
FIG. 1 illustrates the light guiding device according to the present invention.
Figure 2:
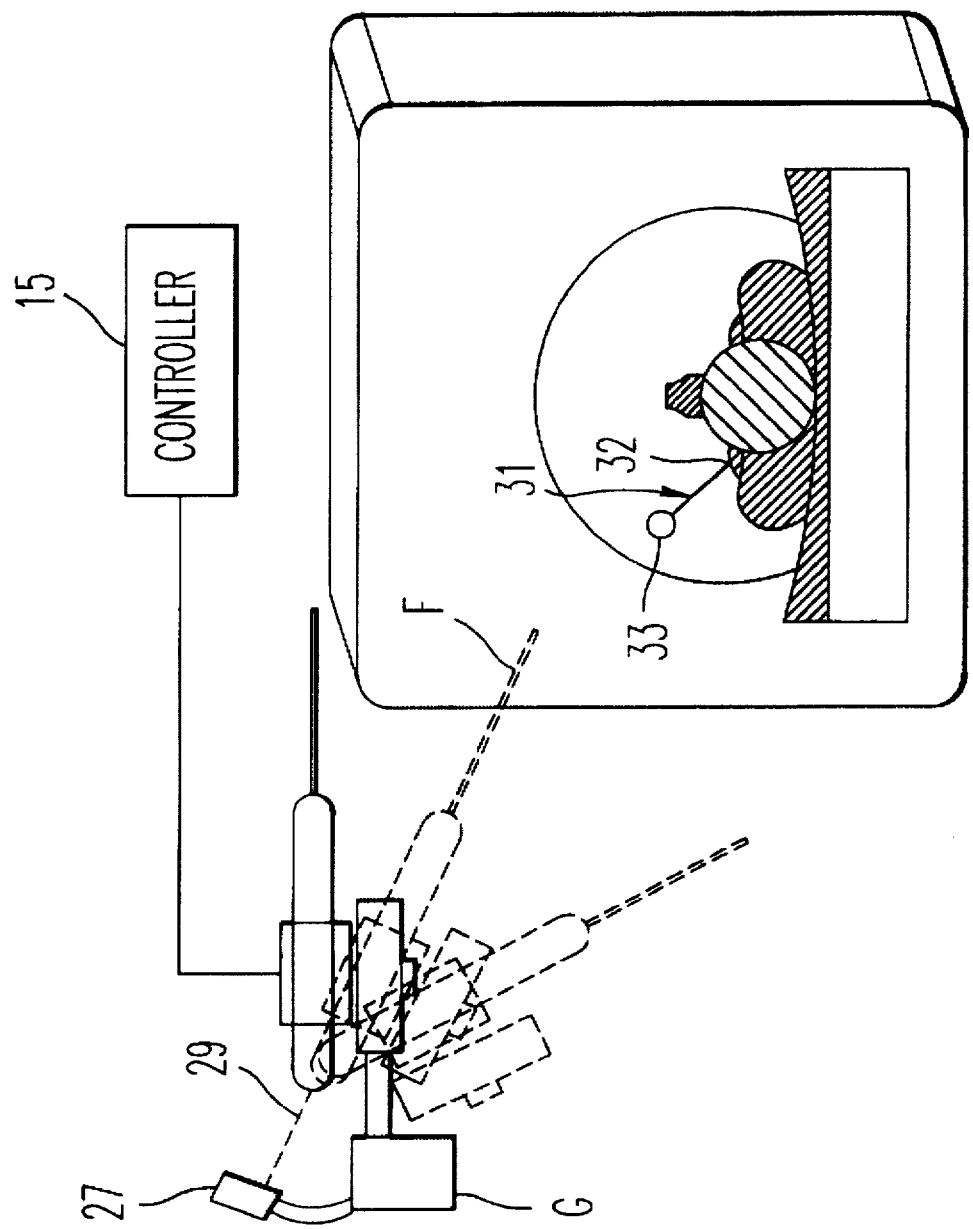
FIG. 2 illustrates the positioning of a mounted guiding system according to FIG. 1 with an infrared reflectance measurement device positioned in proximity to a patient.

Referring now to the drawings, wherein like reference numerals designate identical or corresponding parts throughout the figures, and more particularly to FIG. 1 thereof, there is shown the guiding light device having structural mounting portion G and a laser mount portion A. The laser mount contains the laser B having an illustrated laser beam F. Multi-axial mounting is implemented by X-axis pivot structure C, Y-axis pivot structure D, and Z-axis pivot structure E.

Figure 3:
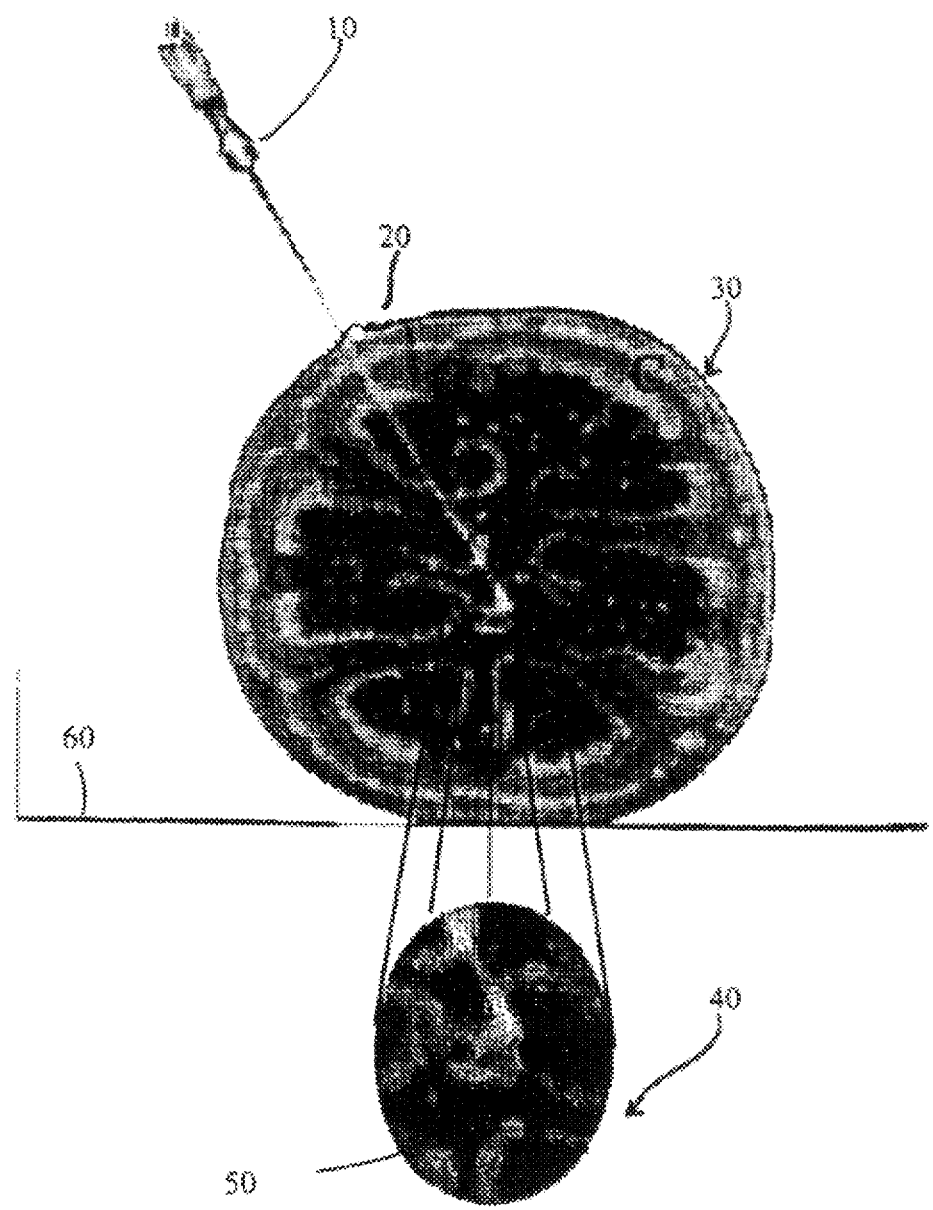
FIG. 3 is an illustration of experiments conducted using the guiding structure of the present invention on an eggplant.

Although shown as operated by controller 15 to orient each of the three axis, the facilitation of remote control of each of these axis in order to have the light positioned in space from a remote terminal is an obvious variation within the scope of the present invention. Likewise the actual movement of the three axis of rotation can be motor controlled in response to the control signals or in any of numerous other ways including the use of memory retention materials. The illustrated controller contains the predetermined three dimensional angle of entry based on the pre-surgery imaging. Furthermore the simultaneous on-line readout with tomographic imaging equipment controlled by means of a joy-stick or a mouse driven operator input is also envisioned as a further enhancement of the video-assisted angle planning. The infrared reflectance measurement device 27 shown as also mounted on the structural mount G provides an IR beam 29 parallel to the laser F. An obvious variation to the IR (infrared) beam includes other forms of coherent or collimated energy in the form of light or sound. An optical processor in the device 27 is programmed with a desired depth of insertion of the surgical device 31 and an audible or visible stimulus is also built into the device 27 to indicate when the desired depth is achieved. An example of an infrared reflectance device is a surveyor's camera which provides a print out of the distance which translates into a depth of penetration when employed in the surgical procedure of the present invention. Experiments with the light guide of the present invention using regular fluoroscopy, C-Arm fluoroscopy, and computer tomography CT are illustrated in FIG. 3. A biopsy needle 10 is shown positioned at the surface entry marker 20 with the guide light being remotely positioned 1.5 meters from the Table 60. The target of this experiment is a plurality of miniature chocolate chips 50 implanted in the eggplant 30. These miniature chocolate chips have a diameter of 2.5 millimeters. The enlargement of the target site 40 illustrates the chocolate chips 50. Repeated trials with multiple approach angles recorded no misses when targeting the small chocolate chip targets.

With the combination of the guiding device and the infrared depth assessment system camera, the procedure to be followed in order to obtain maximum benefit involves acquiring surgical planning images of a patient using either normal Fluoroscopy or C-Arm Fluoroscopy, computer tomography CT, or other imaging devices. Subsequently surgical insertion angles in a three dimensional orthogonal plane are determined as a function of the acquired images. Then the laser is directed to the patient at the spot on their skin where the incision is to be made. Then a distal end 32 of the surgical device 31 is positioned at the light spot on the patient and the proximal end 33 of the surgical device is rotated while maintaining the distal end in a fixed position until the proximal end intercepts the light beam.

The infrared device 27 then provides an initial determination of the distance from the light source to the proximal end 33 of the surgical instrument. Then the distal end 32 of the surgical instrument 31 is inserted into said patient while maintaining the positioning of the light beam on the proximal end 33 of the surgical instrument. When the distance moved by the proximal end reaches a predetermined value indicating the optimum insertion is reached by the surgical device, the infrared device provides an output to cause the surgeon to stop the advance of the surgical instrument.

With this device, precise procedures can be performed at tremendous cost savings in several areas. The most significant cost savings are in the time required for the procedure and the total number of exposures required to confirm instrument position. Furthermore, as a result of the precise positioning, fewer individuals will be needed to perform the procedure. Furthermore the device is small and portable and allows for a location within an imaging environment with substantial ease and allows a positioning so as not to interfere with movement of the surgeon and other personnel involved in the operation.

Obviously, numerous modifications and variations of the present invention are possible in light of the above teachings such as the automated positioning of the device and the use of a digametic indicator on the surgical instrument for mechanically measuring the depth of placement using a dedicated or a remote digital readout. It is therefore to be understood that within the scope of the appended claims, invention may be practiced otherwise than as specifically described herein.

What is claimed as new and is desired to be secured by Letters Patent of the United States is:

1. A multi-axial portable laser aiming device for integrated targeting and entry during surgical procedures, comprising:

a mounting base for positioning on a standard structure;

a laser pivotally mounted on said base;

means for pivoting said laser in each of three orthogonal directions wherein the direction of said beam is controlled by said means for pivoting said laser in said three orthogonal directions; and means for fixing said laser and said beam at a predetermined angle onto a predetermined surface area of a patient whereby said predetermined angle defines the entry site and the entry angle of incision of the patient.

2. A method of tissue incision, comprising the steps of:

acquiring surgical planning images of a patient;

determining surgical insertion angles in a three dimensional orthogonal plane as a function of said acquired images;

positioning a light source in the proximity of said patient whereby a coherent light beam reaches said patient having a predetermined point of incision;

positioning a distal end of a surgical device at said light spot and rotating said surgical device until said light beam strikes a proximal end of said surgical device while maintaining said distal end fixed at said spot;

performing an initial determination of the distance from the light source to said proximal end of said surgical instrument;

inserting said surgical instrument into said patient while maintaining the positioning of said light beam on said proximal end of said surgical instrument;

providing an indication when the distance from the point of insertion to a point inside the body reaches a predetermined value.

3. The aiming device according to claim 1, further comprising a range finder means for determining a depth of insertion of a surgical instrument.

4. The device according to claim 3, wherein said range finding device is positioned to output a beam of light substantially parallel with said laser beam.

5. The portable laser aiming device of claim 1 wherein said laser beam, during incision by a surgical instrument, intersects a proximal end of said surgical instrument and wherein a distal end of said surgical instrument is positioned on said predetermined surface area.

* * * * *